United States Patent
Demssie et al.

(10) Patent No.: US 7,144,922 B2
(45) Date of Patent: Dec. 5, 2006

(54) METHOD AND COMPOUND FOR THE PROPHYLAXIS OR TREATMENT OF AN IMMUNODEFICIENCY CONDITION, SUCH AS AIDS

(75) Inventors: Getachew Demssie, Rockville, MD (US); Seifu M. Belay, Silver Spring, MD (US)

(73) Assignee: Herbal 2000, LLC., Rockville, MD (US)

( * ) Notice: Subject to any disclaimer, the term of this patent is extended or adjusted under 35 U.S.C. 154(b) by 44 days.

(21) Appl. No.: 10/335,737

(22) Filed: Jan. 3, 2003

(65) Prior Publication Data

US 2003/0225159 A1  Dec. 4, 2003

Related U.S. Application Data

(60) Provisional application No. 60/344,055, filed on Jan. 3, 2002.

(51) Int. Cl.
    *A61K 47/30* (2006.01)
(52) U.S. Cl. .................................................. 514/772.3
(58) Field of Classification Search .............. 514/772.3
    See application file for complete search history.

(56) References Cited

U.S. PATENT DOCUMENTS

| 3,833,520 A | | 9/1974 | Tirpak et al. | |
| 5,492,692 A | * | 2/1996 | Digenis et al. | 424/78.25 |
| 5,783,177 A | * | 7/1998 | Greff et al. | 424/78.17 |

\* cited by examiner

*Primary Examiner*—San-Ming Hui
(74) *Attorney, Agent, or Firm*—Dinesh Agarwal, P.C.

(57) ABSTRACT

A method and compound for the prophylaxis or treatment of an immunodeficiency condition, such as acquired immunodeficiency syndrome (AIDS) includes a glycol derivative. More specifically, the glycol derivative includes diethylene glycol dibenzoate.

9 Claims, 4 Drawing Sheets

METHOD AND COMPOUND FOR THE PROPHYLAXIS OR TREATMENT OF AN IMMUNODEFICIENCY CONDITION, SUCH AS AIDS

CROSS-REFERENCE TO RELATED APPLICATIONS

The present application claims priority on prior U.S. Provisional Application Ser. No. 60/344,055, filed Jan. 3, 2002, and which is incorporated herein in its entirety by reference.

BACKGROUND OF THE INVENTION

The present invention is generally directed to the treatment of viral infections, and more particularly to a method and compound for the prophylaxis or treatment of an immunodeficiency condition, such as acquired immunodeficiency syndrome (AIDS).

AIDS has been reported to be first identified in 1981 among homosexual men and intravenous drug users in New York and California. Shortly after its detection in the United States, evidence of AIDS epidemics grew among heterosexual men, women, and children in sub-Saharan Africa. AIDS quickly developed into a worldwide epidemic, affecting virtually every nation. It is reported that by 2000, an estimated 34.7 million adults and 1.4 million children worldwide, had HIV infection or AIDS. The World Health Organization (WHO), a specialized agency of the United Nations (UN), estimates that from 1981 to the end of 2000 about 21.8 million people died as a result of AIDS. More than 4.3 million of those who died were children under the age of 15.

In the United States, about 40,000 new HIV infections occur each year. More than thirty percent of the infections occur in women, and sixty percent occur in ethnic minorities. About 800,000 to 900,000 U.S. residents were infected with HIV, and about 300,000 people were living with full-blown AIDS, in 2000. In Canada, about 4,200 new HIV infections occur each year. About twenty-three percent of these infections occur in women. About 40,000 Canadians were living with HIV infection or full-blown AIDS in 2000.

The incidence of new cases of HIV infections and AIDS deaths has significantly decreased in Canada and the United States since 1995. This decrease is attributed to the availability of new drug treatments and public health programs that target people most at risk for infection. But while the overall rate of HIV infection seems to be on a downturn, certain populations appear to be at greater risk for the disease. In the United States in 1987, Caucasians accounted for sixty percent of AIDS cases, and blacks and Hispanics only thirty-nine percent. But by 2000 the trend had reversed: thirty-eight percent of new cases were diagnosed in Caucasians and sixty-one percent in blacks and Hispanics. Likewise the number of female AIDS patients in the United States has increased significantly in recent years, from seven percent of all AIDS cases in 1985 to thirty percent in 2000. In the United States, African American and Hispanic women accounted for eighty-two percent of AIDS cases among women in 2000.

In western Europe the first cases of AIDS were detected in the early 1980s, and by the late 1990s, at least 30,000 new HIV infections occurred each year. In 2000, more than 540,000 western Europeans were HIV positive, and twenty percent of these cases were women. Before the dissolution of the Union of Soviet Socialist Republics (USSR) in 1991, eastern Europe reported few HIV cases. But since 1995, HIV infection has spread rapidly in cities of several eastern European countries, including Ukraine, Belarus, and Moldova. The WHO estimates that the total number of HIV infections in this region may have risen from less than 30,000 in 1995 to more than 700,000 in 2000.

While cases of AIDS have been reported in every nation of the world, the disease affects some countries more than others. More than ninety-five percent of all HIV-infected people live in the developing world. In these areas, the disease has sapped the populations of young men and women who form the foundation of the labor force. Most die while in the peak of their reproductive years. Moreover, the epidemic has overwhelmed health-care systems, increased the number of orphans, and caused life expectancy rates to plummet. These problems have reached crisis proportions in some parts of the world already burdened by war, political upheaval, or unrelenting poverty.

Nowhere is this better demonstrated than in sub-Saharan Africa, where the number of AIDS cases far exceeds that of all other geographic regions. Of the estimated 16,000 HIV infections that occur each day worldwide, 7,500 of them occur in sub-Saharan Africa. More than seventy percent of all people infected with HIV live in this region. In some countries in the southern part of the continent, including Botswana, Namibia, Swaziland, and Zimbabwe, as much as twenty-five percent of the population has HIV infection or AIDS.

In Asia, the rates of HIV infection remain low relative to many other areas, but the number of reported cases markedly increased in recent years. Health officials fear the virus will affect more people if it spreads through China and India, the world's two most populous countries. For example, 1992 marked the first reported cases of HIV infection in India. By the end of 1999 nearly 4 million adults in India were HIV positive. These cases were mostly confined to 10 of the nation's states, while the remaining 24 states reported low infection rates. HIV infection in India initially was reported primarily in sex workers, but it has quickly spread to the general population in less than five years. Health officials fear that without public education programs, cases of HIV infection will escalate over the next decade, causing the AIDS epidemic in India to dwarf the problems seen in sub-Saharan Africa.

In 2002, the Chinese government reported that China had 850,000 HIV-positive people in a population of more than 1 billion. However, public health experts are concerned by the fast-rising number of new infections among intravenous drug users who share infected needles. In 2000, HIV prevalence among intravenous drug users ranged from forty-four percent to eighty-five percent in selected communities of drug users in both Yunnan, in southern China, and Xinjiang, in northwestern China. The incidence of HIV infection will likely be exacerbated by the growing sex industry in China. Surveys indicate that there are as many as 4 million sex workers in China. Of these, five out of ten never use a condom to protect themselves or their clients from HIV infection or other sexually transmitted infections. In rural areas of China, the incidence of HIV infection is rising because many poverty-stricken people regularly sell their blood. The people who buy the blood use unsterile methods to draw blood, including reusing contaminated needles, which can spread HIV infection.

In Latin America and the Caribbean, region nearly 1.8 million people have been diagnosed with HIV infection or AIDS, twice the incidence in the United States and Canada. In Mexico, 150,000 people have been diagnosed with HIV infection or AIDS, and the disease is the third leading cause of death in men aged 20 to 34. Honduras, which accounts for less than a fifth of the population in Central America, reports more than half of the AIDS cases in that region. In the state of Sao Paolo, Brazil, AIDS has been the leading cause of death among women aged 20 to 34 since 1992.

Historically, the recognized treatment for HIV-1 infection is nucleoside analogs, inhibitors of HIV-1 reverse transcriptase (RT). Intervention with these antiretroviral agents has led to a decline in the number of reported AIDS cases and has been shown to decrease morbidity and mortality associated with advanced AIDS. Prolonged treatment with these reverse transcriptase inhibitors eventually leads to the emergence of viral strains resistant to their antiviral effects. Recently, inhibitors of HIV-1 protease have emerged as a new class of HIV-1 chemotherapy. HIV-1 protease is an essential enzyme for viral infectivity and replication. Protease inhibitors have exhibited greater potency against HIV-1 in vitro than nucleoside analogs targeting HIV-1 RT. Inhibition of HIV-1 protease disrupts the creation of mature, infectious virus particles from chronically infected cells. This enzyme has become a viable target for therapeutic intervention and a candidate for combination therapy.

Knowledge of the structure of the HIV-1 protease also has led to the development of novel inhibitors, such as saquinovir, ritonavir, indinivir and nelfinavir. NNRTIs (non-nucleoside reverse transcriptase inhibitors) have recently gained an increasingly important role in the therapy of HIV infection. Several NNRTIs have proceeded onto clinical development (i.e., tivirapine, loviride, MKC-422, HBY-097, DMP 266). Nevirapine and delaviridine have already been authorized for clinical use. Every step in the life cycle of HIV-1 replication is a potential target for drug development.

Unfortunately, however, the single targeted approach as stated above, has only been able to target RT or PR enzymes. As a result, this approach has favored the virus natural selection to evade drug therapy by mutating at a single or few amino acid sequences. According to a CDC report (December 2001), 75% mortality rate in HIV-1 patients is co-related to drug resistant HIV variants. The search for new antiretroviral effective drug against HIV-1 resistant variants has dramatically increased.

Many of the antiretroviral drugs currently used in chemotherapy either are derived directly from natural products, or are synthetics based on a natural product model. The rationale behind the inclusion of deoxynucleoside as a natural based antiviral drugs originated in a series of publications dating back as early as 1950, wherein the discovery and isolation of thymine pentofuranoside from the air-dried sponges (cryptotethia crypta) of the Bahamas was reported. A significant number of nucleosides were made with regular bases but modified sugars, or both acyclic and cyclic derivatives, including AZT and acyclovir. The natural spongy-derived product led to the first generation, and subsequent second—third generations of nucleosides (AZT, DDI,DDC, D4T,3TC) antivirals specific inhibitors of HIV-1 RT.

A number of non-nucleoside agents (NNRTIs) have been discovered from natural products that inhibit RT allosterically. NNRTIs have considerable structural diversity but share certain common characteristics in their inhibitory profiles. Among NNRTIs isolated from natural products include: calanoid A from calophylum langirum; Triterpines from Maporonea African a. There are publications on natural HIV integrase inhibitors from the marine ascidian alkaloids, the lamellarin.

The role of HIV protease in the production of functionally infectious particle has been described as a critical process for retrovirus as well as HIV replication. The natural product, Pepstatin A, is a metabolite of streptomycin testaceus and Streptomyces argentolus var. toyonakensis was shown to inhibit HIV-1 Protease enzyme. The key strategy used in the development of the current HIV-1 protease inhibitors was to substitute the scissile P1-P1 amide bond by a non-hydrozable isoster with tetrahedral geometry; the designs were guided by assays and based on substrate specificity. It eventually led to the optimization of peptidomimetric lead structure and the development of novel class of protease inhibitors including indinvir, Saqunovir, nelfinavir and retinovir.

In Ethiopia, there are currently more than 3 million adults and close to 1 million children infected with HIV-1. The rate of HIV-1 vertical and horizontal transmission has drastically increased over the years. More than 50% of the nation's available hospital beds are over crowded with HIV-1 patients, and 99.9% of the HIV-1 patients cannot afford the commercially available antiretroviral drugs. Even for those who can afford it (<0.1%) there is no HIV-1 staging or managing infrastructure to evaluate therapeutic indices. The national health status is in a state of emergency that could cripple the national economy and decimate the younger generations. Unless immediate therapeutic and behavioral interventions are expedited, the exponential rate of HIV-1 growth and related morbidity could easily reach 6 million by the year 2005. This is a deadly reality that Ethiopians, Ethiopian HIV-1 experts, and the world at large are currently confronted with.

In order to provide therapeutic intervention to 400,000 AIDS infected patients with the commercially available drugs, the country of Ethiopia alone will have to spend close to 2 billion dollars a year. This figure does not include other concomitant drugs needed for TB, abdominal fungus, pneumonia, toxic effects caused by drugs and monthly patient evaluation for therapeutic index and HIV-1 dose response assessments. This approach is simply way beyond the GNP of Ethiopia.

The other serious problem arising from importing and prescribing non-HHART (highly active retrovirus therapy) drug treatments in Ethiopia is the creation of fertile environment for the emergence of highly virulent, resistant viruses. More than 75% of AIDS therapeutic failure is caused by resistance viruses. A centralized data bank and HIV-1 management team is crucial to monitor the success or failure of antiretroviral therapy. Salvage therapy with the commercial drugs, triple or quadruple combination is essential to reach effective clinical diagnostic therapeutic index. This again could bankrupt the economy of Ethiopia.

In view of the drawbacks associated with conventional remedies and the growing worldwide concern for the AIDS epidemic, there is a need for a remedy which is inexpensive, less toxic, potent, and easily available. In this regard, the inventors of the present invention believe that the compound or antiviral agent of the invention, H2K1001(90l or 90i), would be a perfect alternative since it is less costly, highly potent, easy to deliver to AIDS patients, and highly active against resistant viruses. In addition, the compound of the invention is a simple multi-charged molecule that could be manufactured at low cost. Consequently, the cost of the drug would be affordable to the majority of AIDS patients in Ethiopia and other developing countries.

OBJECTS AND SUMMARY OF THE INVENTION

The principal object of the present invention is to provide a method and compound for the prophylaxis or treatment of an immunodeficiency condition, such as acquired immunodeficiency syndrome (AIDS).

An object of the present invention is to provide a method and compound for the prophylaxis or treatment of an immunodeficiency condition, such as acquired immunodeficiency syndrome (AIDS), wherein the compound is less toxic and more potent at lower doses (or lower concentrations) than the conventional compounds.

Another object of the present invention is to provide a method and compound for the prophylaxis or treatment of an immunodeficiency condition, such as acquired immunodeficiency syndrome (AIDS), wherein the compound is effective in advanced, as well as in early stages of the condition or infection.

An additional object of the present invention is to provide a method and compound for controlling or arresting replication of an immunodeficiency virus, such as human immunodeficiency virus (HIV).

Yet an additional object of the present invention is to provide a method and compound for the prophylaxis or treatment of an immunodeficiency condition, such as acquired immunodeficiency syndrome (AIDS), wherein the compound comprises an herbal extract. The extract includes a glycol derivative. More specifically, the glycol derivative includes diethylene glycol dibenzoate.

Still yet an additional object of the present invention is to provide a method and compound for the prophylaxis or treatment of an immunodeficiency condition, such as acquired immunodeficiency syndrome (AIDS), which includes a glycol derivative. More specifically, the glycol derivative includes diethylene glycol dibenzoate.

A further object of the present invention is to provide a method and compound for the prophylaxis or treatment of an immunodeficiency condition, such as acquired immunodeficiency syndrome (AIDS), which are inexpensive, highly potent, easy to administer to the patients, highly active against the resistant virus, and easy to manufacture.

In accordance with the present invention, a compound for the prophylaxis or treatment of an infection or condition caused by an immunodeficiency virus, includes a glycol derivative. More specifically, the glycol derivative includes diethylene glycol dibenzoate.

In accordance with the present invention, a method for the prophylaxis or treatment of an infection or condition caused by an immunodeficiency virus, includes administering to a subject in need thereof a compound including a glycol derivative. More specifically, the glycol derivative includes diethylene glycol dibenzoate.

In summary, the compound of the invention, H2K1001 (90l or 90i) is a highly potent new antiretroviral drug or agent that works against resistant HIV viruses. Initial evaluation of this compound in the CEMSS cell line demonstrated significant antiviral activity against the RF laboratory strain of HIV-1. The purified fraction 90l (or 90i) yielded a 50% effective concentration (EC50) of 0.02 ug/ml. At the same time, there was no discernible drug induced toxicity in this study (50% inhibitory concentration, IC50, was greater than the high test concentration of 100 ug/ml). The resulting therapeutic index (TI=IC50/EC50) of greater than 5000 suggests a highly active compound. Testing in PBMC against primary clinical isolates of HIV-1 P2, which is resistant to a variety of non-nucleoside inhibitors or HIV-1 reverse transcriptase. Also, the inventive compound (H2K1001(90l or 90i)) produced an EC50 of 0.8 ug/ml, an IC50 greater than 100, and a TI of greater than 125.

BRIEF DESCRIPTION OF THE DRAWINGS

The above and other objects, novel features and advantages of the present invention will become apparent from the following detailed description of the invention, as illustrated in the drawings, in which.

DETAILED DESCRIPTION OF THE INVENTION

Figure 1:
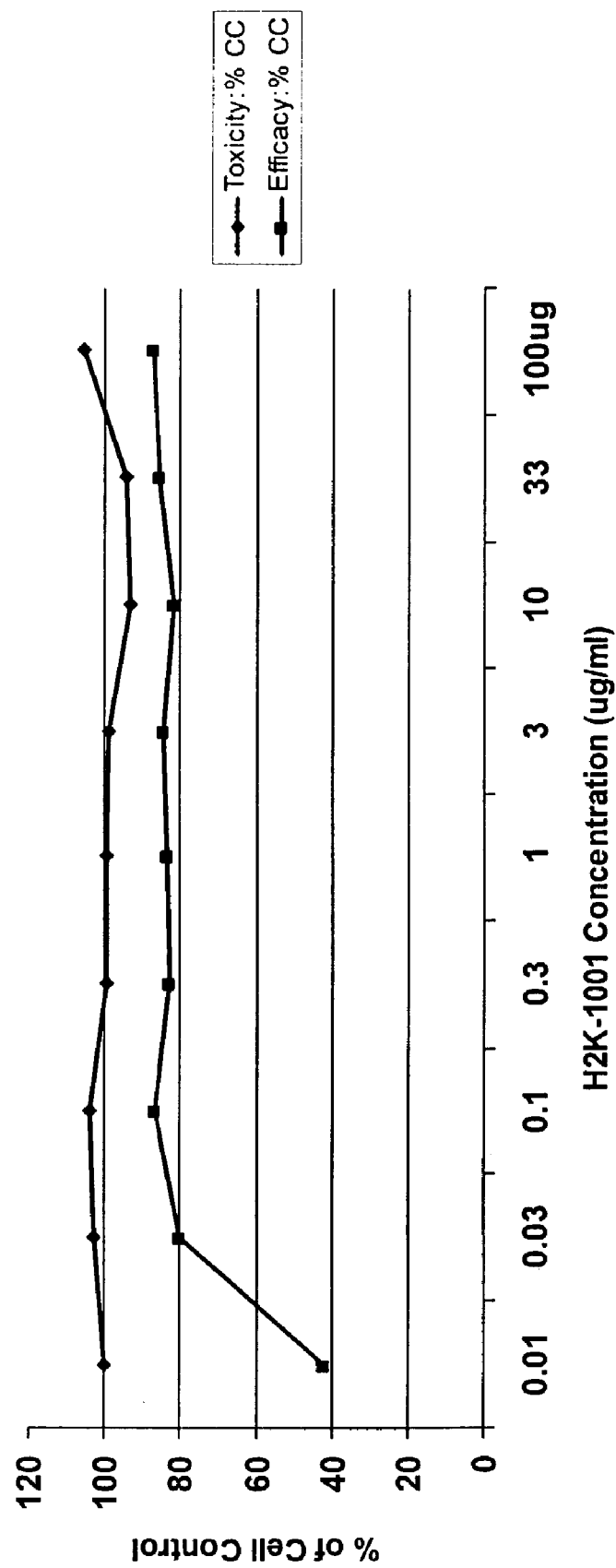
FIG. 1 is a graphical representation illustrating the effect of the compound of the present invention, H2K1001(90l or 90i), on HIV-1 in CEM-SS T-lymphoblastoid cells.

The present invention is based on the discovery that an herbal extract, which includes a glycol derivative, is effective against HIV virus. More specifically, we found that the extract includes diethylene glycol dibenzoate, which in vitro testing showed to be effective against HIV-1 virus.

We examined the antiviral activity of an antiviral agent or compound that we designated as 90l (or 90i) derived from an extract of an herbal mixture that we designated as H2K1001, against the RF laboratory strain of HIV-1 in CEM-SS T-lymphoblastoid cells, and against a nucleoside and non-nucleoside resistant clinical isolate of HIV-1 (P2) in peripherial blood mononuclear cells (PBMC). A brief description of each assay employed is discussed below.

H2K1001(90l or 90i) is a natural product that was isolated by bioassay guided fractionations, and further purified, molecularly characterized and tested against variety of HIV-1 strains.

Antiviral Drug Assay in CEM-SS Cells

This assay was used to test the effectiveness of anti-HIV drug monotherapy in the established T-cell line CEM-SS infected with HIV-$1_{RF}$, HIV-$1_{IIIb}$, HIV-$2_{ROD}$, or other cytolytic variants of HIV. The antiviral agent and control (known antiviral drug—AZT) efficacy and cytotoxicity were determined by the metabolic reduction of the tetrazolium salt MTS (available from Promega).

Drug and Cell Preparation

The drugs were solubilized in DMSO (dimethyl sulfoxide). Three to ten vials of the antiviral agent and AZT were prepared and maintained at −70° C. CEM-SS cells were in logarithmic growth phase at the time of experimentation. Virus (HIV-$1_{RF}$) stocks that past the necessary quality controls (killing effect on the type of cells used, limited variability, etc) were thawed and maintained on ice until required for addition.

Test Plates

Half-log serial dilutions of the antiviral agent or compound of the invention, H2K1001 (90i), were made in tissue culture media (RPMI 1640 without phenol red, supplemented with 10% heat inactivated fetal bovine serum, 1% L-Glutamine, 1% Pen/Strep and 50 ug/ml gentimycin).

Virus, cell, drug and diluent (ethanol) controls were included for these tests. Virus was added after cells and drugs were mixed. Cell, drug, and virus containing cultures were incubated for six (6) days without additional feeding at which time the cultures were evaluated macrosopically and microscopically for cell toxicity, and the tetrazolium salt MTS was added for quantitation by the colorimetric determination of formazan production (optical density).

Endpoint Determinations

Drug efficacy and cytotoxicity effects were determined six days after infection by the metabolic reduction of the tetrazolium salt XTT to its' formazan by surviving cells and was quantitated by determination of optical density at 450 nm with background subtraction at 650 nm (Tables 1–4).

Results

The drug plate analysis reports from this assay are provided below in Tables 1–4. Calculated endpoints (EC50, etc.) were determined using Cho and Cho Median Effect Equation (Daids Virology Manual for HIV Laboratories, Compiled by The Division of Aids, National Institute of Allergy and Infectious Diseases, National Institutes of Health and Collaborating Investigators, Version January 1997).

Figure 2:
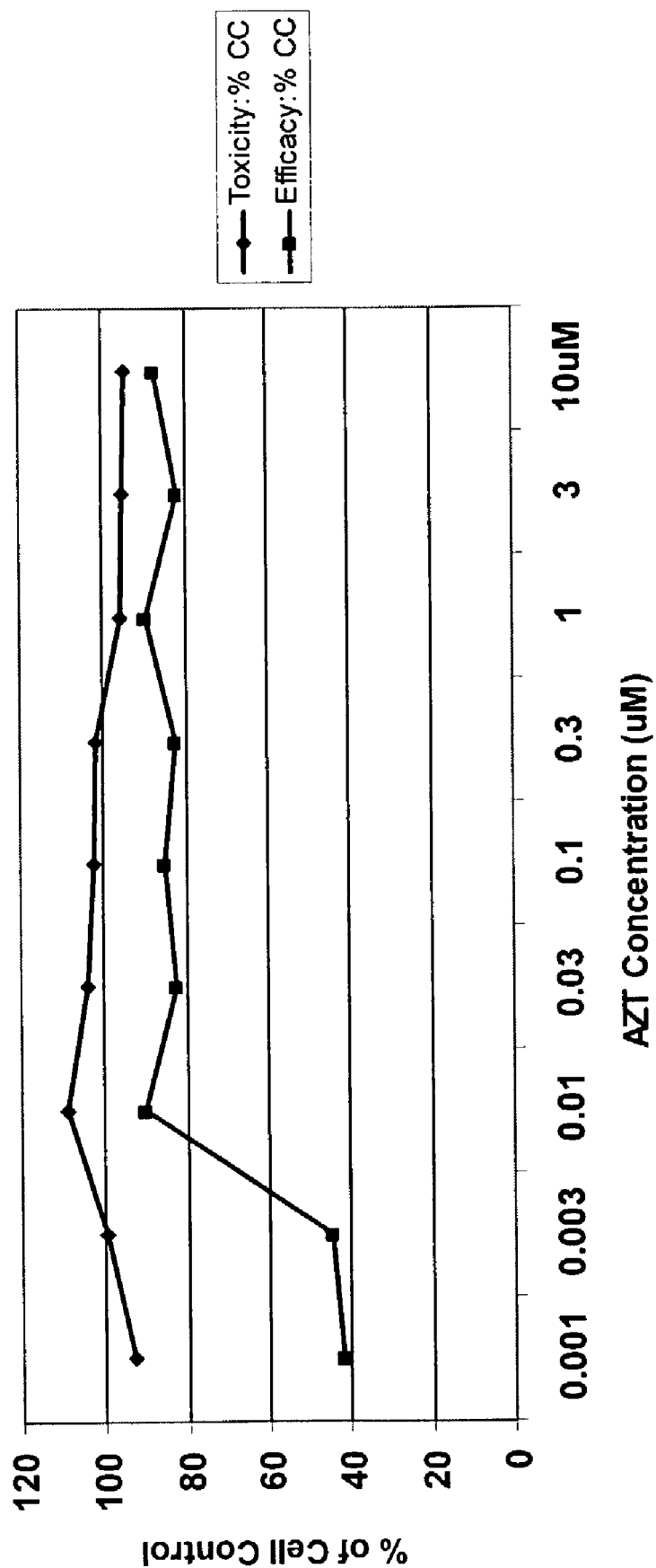
FIG. 2 is a graphical representation illustrating the effect of control compound (AZT) on HIV-1 in CEM-SS T-lymphoblastoid cells.

FIGS. 1–2 are graphical representations illustrating the effects of the compound of the present invention and the control drug (AZT), respectively, on HIV-1 in CEM-SS T-lymphoblastoid cells. Tables 5–6 provide the data plotted in FIGS. 1–2, respectively.

Initial evaluation of 90i, the antiviral agent of the invention, in the CEM-SS cell line, demonstrated significant antiviral activity against the RF laboratory strain of HIV-1. The antiviral agent yielded a 50% effective concentration ($EC_{50}$) of approximately 0.020 ug/ml (see Table 1). At the same time, there was no discernible drug induced toxicity in this study (50% inhibitory concentration, $IC_{50}$, was greater than the high test concentration of 100 ug/ml) (see Table 2). The resulting therapeutic index ($TI=IC_{50}/EC_{50}$) of greater than 5000 suggests a highly active compound, at least in vitro. The AZT control in our study (included to ensure the functionality of all antiviral testing) yielded an $EC_{50}$ of approximately 0.0035 uM (see Table 3), an $IC_{50}$ greater than 10 uM and a TI of greater than 2857 (see Table 4).

TABLE 1

Efficacy Testing Data for H2K1001 (90i) in CEM-SS T-Lymphoblastoid Cells Versus HIV-1 (RF)

|  | 100* | 33* | 10* | 3* | 1* | 0.3* | 0.1* | 0.03* | 0.01* | VC* |
|---|---|---|---|---|---|---|---|---|---|---|
|  | 2.2450 | 2.1945 | 2.0385 | 2.2490 | 2.2771 | 2.1099 | 2.2196 | 2.0839 | 0.9892 | 0.5222 |
|  | 1.9588 | 1.9560 | 2.0038 | 1.9311 | 1.9106 | 1.8158 | 2.0140 | 1.6926 | 1.0238 | 0.5293 |
|  | 2.1625 | 2.0909 | 1.8968 | 1.9576 | 1.8914 | 2.1016 | 2.0883 | 2.0343 | 1.0477 | 0.4715 |
| Mean | 2.1221 | 2.0805 | 1.9797 | 2.0459 | 2.0264 | 2.0091 | 2.1073 | 1.9369 | 1.0202 | 0.5077 |
| +/−SD | 0.1473 | 0.1196 | 0.0739 | 0.1764 | 0.2174 | 0.1675 | 0.1041 | 0.2130 | 0.0294 | 0.0315 |
| CV | 0.0694 | 0.0575 | 0.0373 | 0.0862 | 0.1073 | 0.0833 | 0.0494 | 0.1100 | 0.0288 | 0.0621 |
| % CC | 88 | 86 | 82 | 84 | 84 | 83 | 87 | 80 | 42 | 21 |

*Drug Concentration in ug/ml.
SD = Standard Deviation.
CV = Coefficient of Variation.
CC = Cell Control.
VC = Virus Control.

TABLE 2

Toxicity Testing Data for H2K1001 (90i) in CEM-SS T-Lymphoblastoid Cells Versus HIV-1 (RF)

|  | 100* | 33* | 10* | 3* | 1* | 0.3* | 0.1* | 0.03* | 0.01* | CC* |
|---|---|---|---|---|---|---|---|---|---|---|
|  | 2.3986 | 2.3330 | 1.9415 | 2.0028 | 2.0248 | 1.8679 | 2.3026 | 2.1542 | 2.2494 | 2.0675 |
|  | 2.6684 | 2.2031 | 2.5097 | 2.5800 | 2.6325 | 2.6984 | 2.5829 | 2.6984 | 2.5627 | 2.5950 |
|  | 2.6143 | 2.3276 | 2.3457 | 2.6192 | 2.5957 | 2.6727 | 2.6592 | 2.6382 | 2.4831 | 2.6080 |
| Mean | 2.5604 | 2.2879 | 2.2656 | 2.4007 | 2.4177 | 2.4130 | 2.5149 | 2.4969 | 2.4317 | 2.4235 |
| +/−SD | 0.1427 | 0.0735 | 0.2924 | 0.3451 | 0.3407 | 0.4722 | 0.1878 | 0.2983 | 0.1628 | 0.3084 |
| CV | 0.0557 | 0.0321 | 0.1291 | 0.1438 | 0.1409 | 0.1957 | 0.0747 | 0.1195 | 0.0670 | 0.1272 |
| % CC | 106 | 94 | 93 | 99 | 100 | 100 | 104 | 103 | 100 | 100 |

*Drug Concentration in ug/ml.

TABLE 3

Efficacy Testing Data for AZT in CEM-SS T-Lymphoblastiod Cells Versus HIV-1 (RF)

|  | 10+ | 3+ | 1+ | 0.3+ | 0.1+ | 0.03+ | 0.01+ | 0.003+ | 0.001+ | VC+ |
|---|---|---|---|---|---|---|---|---|---|---|
|  | 1.8513 | 1.9038 | 1.9616 | 1.9402 | 1.8079 | 1.6606 | 1.8216 | 0.8944 | 0.9015 | 0.4326 |
|  | 1.8922 | 1.8368 | 2.0118 | 1.7198 | 2.1031 | 1.7129 | 1.5744 | 0.9499 | 0.8874 | 0.4464 |
|  | 2.0748 | 1.7308 | 1.9864 | 1.8287 | 1.7718 | 2.1320 | 2.5998 | 1.1112 | 0.9820 | 0.4401 |
| Mean | 1.9394 | 1.8238 | 1.9866 | 1.8296 | 1.8943 | 1.8352 | 1.9986 | 0.9852 | 0.9236 | 0.4397 |

TABLE 3-continued

Efficacy Testing Data for AZT in CEM-SS T-Lymphoblastiod Cells Versus HIV-1 (RF)

|  | 10+ | 3+ | 1+ | 0.3+ | 0.1+ | 0.03+ | 0.01+ | 0.003+ | 0.001+ | VC+ |
|---|---|---|---|---|---|---|---|---|---|---|
| +/−SD | 0.1190 | 0.0872 | 0.0251 | 0.1102 | 0.1818 | 0.2584 | 0.5351 | 0.1126 | 0.0510 | 0.0069 |
| CV | 0.0614 | 0.0478 | 0.0126 | 0.0602 | 0.0959 | 0.1408 | 0.2677 | 0.1143 | 0.0553 | 0.0157 |
| % CC | 87 | 82 | 90 | 82 | 85 | 83 | 90 | 44 | 42 | 20 |

+Drug Concentration in uM.

TABLE 4

Toxicity Testing Data for AZT in CEM-SS T-Lymphoblastiod Cells Versus HIV-1 (RF)

|  | 10+ | 3+ | 1+ | 0.3+ | 0.1+ | 0.03+ | 0.01+ | 0.003+ | 0.001+ | CC+ |
|---|---|---|---|---|---|---|---|---|---|---|
|  | 2.2320 | 2.0757 | 1.8131 | 1.6316 | 1.7705 | 2.5696 | 2.1282 | 2.2086 | 1.6705 | 2.0101 |
|  | 2.1655 | 2.3508 | 2.4605 | 2.9433 | 2.6402 | 2.2796 | 2.6386 | 2.3516 | 2.1309 | 2.1129 |
|  | 1.9163 | 1.9144 | 2.1094 | 2.2144 | 2.3896 | 2.0840 | 2.4680 | 2.0717 | 2.3829 | 2.5305 |
| Mean | 2.1046 | 2.1136 | 2.1277 | 2.2631 | 2.2668 | 2.3111 | 2.4116 | 2.2106 | 2.0614 | 2.2178 |
| +/−SD | 0.1664 | 0.2207 | 0.3241 | 0.6572 | 0.4477 | 0.2443 | 0.2598 | 0.1400 | 0.3612 | 0.2756 |
| CV | 0.0791 | 0.1044 | 0.1523 | 0.2904 | 0.1975 | 0.1057 | 0.1077 | 0.0633 | 0.1752 | 0.1243 |
| % CC | 95 | 95 | 96 | 102 | 102 | 104 | 109 | 100 | 93 | 100 |

+Drug Concentration in uM.

TABLE 5

Effect of H2K-1001 on HIV-1 (RF) in CEM-SS Cells

| H2K-1001 (ug/ml) | Toxicity % CC | Efficacy % CC |
|---|---|---|
| 0.01 | 100 | 42 |
| 0.03 | 103 | 80 |
| 0.1 | 104 | 87 |
| 0.3 | 100 | 83 |
| 1 | 100 | 84 |
| 3 | 99 | 84 |
| 10 | 93 | 82 |
| 33 | 94 | 86 |
| 100 ug | 106 | 88 |

TABLE 6

Effect of AZT on HIV-1 (RF) in CEM-SS Cells

| AZT Concentration (uM) | Toxicity % CC | Efficacy % CC |
|---|---|---|
| 0.001 | 93 | 42 |
| 0.003 | 100 | 44 |
| 0.01 | 109 | 90 |
| 0.03 | 104 | 83 |
| 0.1 | 102 | 85 |
| 0.3 | 102 | 82 |
| 1 | 96 | 90 |
| 3 | 95 | 82 |
| 10 uM | 95 | 87 |

Antiviral Drug Assay in PBMC

This assay was used to test the effectiveness of anti-HIV drug monotherapy in peripheral blood mononuclear cells (PBMC) infected with clinical isolates of HIV-1. Drug efficacy was determined by the production of supernatant HIV-1 p24. Drug-induced cytotoxicity was determined by the metabolic reduction of tetrazolium salts (MTS; Promega).

Drug and Cell Preparation

The antiviral drug or agent of the invention, H2K-1001 (90i), was solubilized. PBMCs, stimulated with PHA (phytohemagglutinin) for three days were employed throughout. Virus stocks (U.S. Clinical isolates) grown in PBMCs only, that past the necessary quality controls (i.e., replicate to high titer in PBMCs and meet the requirements as to genotype and phenotype) were rapidly thawed and maintained on ice until required for infection.

Test Plates

Half-log serial dilutions of test drugs and controls were prepared in tissue culture media (RPMI 1640 without phenol red, supplemented with 10% heat inactivated fetal bovine serum, 1% L-Glutamine, 1% Pen/Strep and 50 µg/ml gentamicin). Virus and cell controls were included on each test plate. Virus was added after cells and drugs were mixed. Cell, drug and virus containing cultures were incubated for seven (7) days with an interim feeding at day three or four.

Endpoint Determinations (Sample Harvest, p24 Quantitation and Cell Viability)

Supernatants were sampled at seven days for p24 determination by antigen capture ELISA. Cytotoxicity was measured by the metabolic reduction of the tetrazolium salt according to the manufacturer's (Promega) recommendations.

Results

The drug analysis reports from these studies are provided below in Tables 7–10. Efficacy ($EC_{50}$) and viability ($IC_{50}$) determinations were made using Cho and Cho Median Effect Equation, as noted above. Efficacy is expressed as the 50% effective concentration ($EC_{50}$) and drug induced toxicity as the 50% inhibitory concentration ($IC_{50}$).

Figure 3:
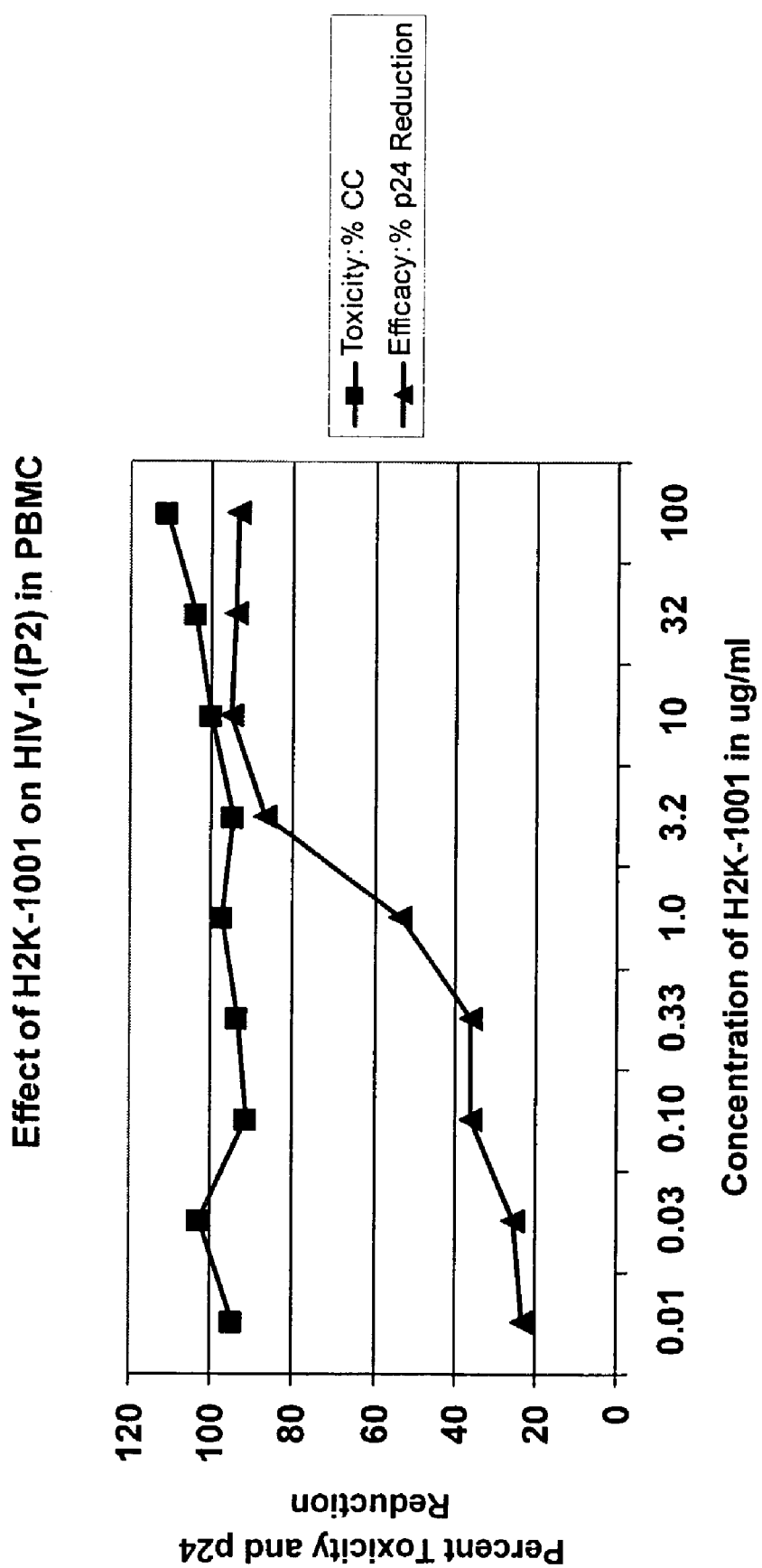
FIG. 3 is a graphical representation illustrating the effect of the compound of the present invention, H2K1001(90l or 90i), on HIV-1(P2) in peripheral blood nonnuclear cells (PBMC)
Figure 4:
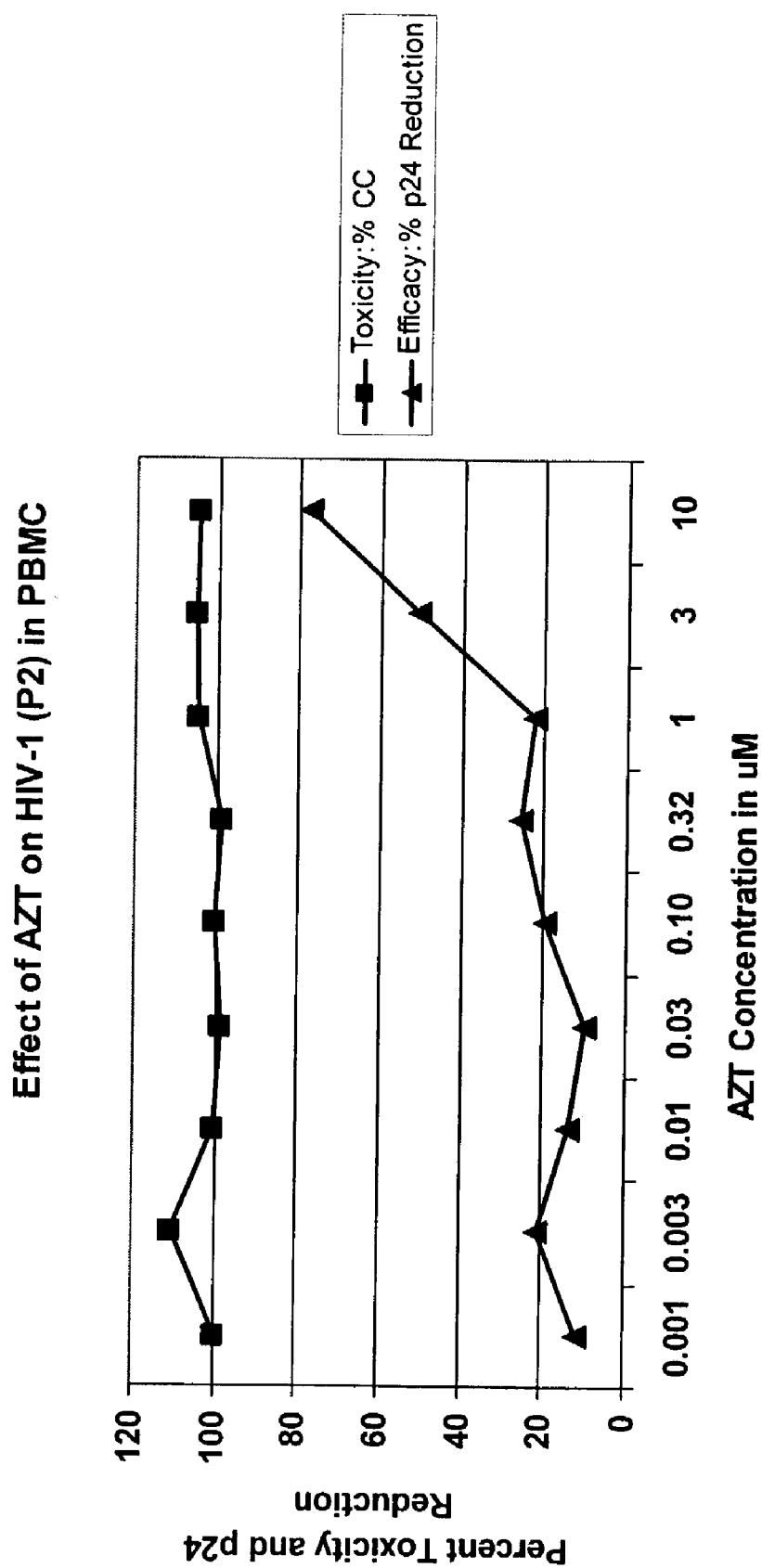
FIG. 4 is a graphical representation illustrating the effect of control compound (AZT) on HIV-1 in PBMC.

FIGS. 3–4 are graphical representations illustrating the effects of the compound of the invention and the control drug (AZT), respectively, on HIV-1 in PBMC. Tables 11–12 provide data plotted in FIGS. 3–4, respectively.

Testing in PBMCs was directed against a primary clinical isolate of HIV-1 P2, which is resistant to a variety of non-nucleoside inhibitors or HIV-1 reverse transcriptase and, in our hands, AZT. Testing AZT (control) against this virus, as expected, produced a relatively high $EC_{50}$ of 3 uM. Typically AZT produces $EC_{50}$s of less than 0.01 uM in studies of susceptible isolates in PBMCs. In this case, 90i produced an $EC_{50}$ of approximately 0.8 ug/ml, an $IC_{50}$, again, greater than 100 ug/ml and a TI of greater than 125.

TABLE 7

Efficacy Testing Data For Determination of H2K-1001 (90i) Suppression of P2 Replication in PBMC

|  | 100* | 32* | 10* | 3* | 1* | 0.33* | 0.10* | 0.03* | 0.01* | VC* |
|---|---|---|---|---|---|---|---|---|---|---|
|  | 0.1530 | 0.1070 | 0.1090 | 0.4510 | 1.4266 | 1.9451 | 1.9461 | 2.1210 | 2.1000 | 2.8731 |
|  | 0.1820 | 0.1823 | 0.1226 | 0.3219 | 1.4567 | 1.7120 | 1.8101 | 1.9460 | 2.2130 | 2.9430 |
|  | 0.2488 | 0.2177 | 0.1874 | 0.3410 | 1.1116 | 1.8460 | 1.7450 | 2.3450 | 2.2937 | 2.7600 |
| Mean | 0.1946 | 0.1690 | 0.1397 | 0.3713 | 1.3316 | 1.8344 | 1.8337 | 2.1373 | 2.2022 | 2.8587 |
| +/−SD | 0.0491 | 0.0565 | 0.0419 | 0.0697 | 0.1911 | 0.1170 | 0.1026 | 0.2000 | 0.0973 | 0.0923 |
| CV | 0.2525 | 0.3345 | 0.3000 | 0.1877 | 0.1435 | 0.0638 | 0.0560 | 0.0936 | 0.0442 | 0.0323 |
| % p24 Red. | 93 | 94 | 95 | 87 | 53 | 36 | 36 | 25 | 23 | 0 |

*Drug Concentration in ug/ml.

TABLE 8

Efficacy Testing Data for AZT Suppression of P2 Replication in PBMC

|  | 10+ | 3+ | 1+ | 0.32+ | 0.10+ | 0.03+ | 0.01+ | 0.003+ | 0.001+ | VC+ |
|---|---|---|---|---|---|---|---|---|---|---|
|  | 0.5641 | 1.5431 | 2.2341 | 2.1786 | 2.2341 | 2.4310 | 2.5410 | 1.9152 | 2.6267 | 2.8460 |
|  | 0.7416 | 1.3421 | 2.1455 | 2.3410 | 2.3519 | 2.5610 | 2.4671 | 2.8470 | 2.6849 | 2.9845 |
|  | 0.6745 | 1.4541 | 2.4364 | 2.0013 | 2.4781 | 2.9461 | 2.5674 | 2.1478 | 2.4510 | 2.9541 |
| Mean | 0.6601 | 1.4464 | 2.2720 | 2.1736 | 2.3547 | 2.6460 | 2.5252 | 2.3033 | 2.5875 | 2.9282 |
| +/−SD | 0.0896 | 0.1007 | 0.1491 | 0.1699 | 0.1220 | 0.2679 | 0.0520 | 0.4850 | 0.1218 | 0.0728 |
| CV | 0.1358 | 0.0696 | 0.0656 | 0.0782 | 0.0518 | 0.1012 | 0.0206 | 0.2106 | 0.0471 | 0.0249 |
| % p24 Red. | 77 | 51 | 22 | 26 | 20 | 10 | 14 | 21 | 12 | 0 |

+Drug Concentration in uM.

TABLE 9

Toxicity Testing Data for H2K-1001 (90i) in PBMC Versus P2

|  | 100* | 32* | 10* | 3* | 1* | 0.33* | 0.10* | 0.03* | 0.01* | CC* |
|---|---|---|---|---|---|---|---|---|---|---|
|  | 2.0185 | 1.4668 | 1.4284 | 1.3251 | 1.2837 | 1.2798 | 1.2144 | 1.6969 | 1.2592 | 1.3431 |
|  | 1.3311 | 1.4605 | 1.3205 | 1.2861 | 1.3403 | 1.2969 | 1.2409 | 1.4163 | 1.3126 | 1.4270 |
|  | 1.2797 | 1.4115 | 1.4232 | 1.3193 | 1.4183 | 1.3210 | 1.3410 | 1.1816 | 1.3623 | 1.3949 |
| Mean | 1.5431 | 1.4463 | 1.3907 | 1.3102 | 1.3474 | 1.2992 | 1.2654 | 1.4316 | 1.3114 | 1.3883 |
| +/−SD | 0.4125 | 0.0303 | 0.0609 | 0.0210 | 0.0676 | 0.0207 | 0.0668 | 0.2580 | 0.0516 | 0.0423 |
| CV | 0.2673 | 0.0209 | 0.0438 | 0.0161 | 0.0502 | 0.0159 | 0.0528 | 0.1802 | 0.0393 | 0.0305 |
| % CC | 111 | 104 | 100 | 94 | 97 | 94 | 91 | 103 | 94 | 100 |

*Drug Concentration in ug/ml.

TABLE 10

Toxicity Testing Data for AZT in PBMC Versus P2

|  | 10+ | 3+ | 1+ | 0.32+ | 0.10+ | 0.03+ | 0.01+ | 0.003+ | 0.001+ | CC+ |
|---|---|---|---|---|---|---|---|---|---|---|
|  | 1.4841 | 1.5385 | 1.4673 | 1.2854 | 1.3539 | 1.2997 | 1.2749 | 1.3087 | 1.3486 | 1.3587 |
|  | 1.3359 | 1.3532 | 1.3462 | 1.3284 | 1.3060 | 1.2844 | 1.2977 | 1.3790 | 1.3251 | 1.3865 |
|  | 1.4174 | 1.3718 | 1.4308 | 1.3918 | 1.4174 | 1.4185 | 1.4911 | 1.8126 | 1.3814 | 1.3098 |
| Mean | 1.4125 | 1.4212 | 1.4148 | 1.3352 | 1.3591 | 1.3342 | 1.3546 | 1.5001 | 1.3517 | 1.3517 |
| +/−SD | 0.0742 | 0.1020 | 0.0621 | 0.0535 | 0.0559 | 0.0734 | 0.1188 | 0.2729 | 0.0283 | 0.0388 |
| CV | 0.0525 | 0.0718 | 0.0439 | 0.0401 | 0.0411 | 0.0550 | 0.0877 | 0.1819 | 0.0209 | 0.0287 |
| % CC | 104 | 105 | 105 | 99 | 101 | 99 | 100 | 111 | 100 | 100 |

+Drug Concentration in uM.

TABLE 11

Effect of H2K-1001 on HIV-1 (P2) in PBMC

| H2K-1001 (ug/ml) | Toxicity % CC | Efficacy % p24 Reduction |
|---|---|---|
| 0.01 | 94 | 23 |
| 0.03 | 103 | 25 |
| 0.10 | 91 | 36 |
| 0.33 | 94 | 36 |
| 1.0 | 97 | 53 |
| 3.2 | 94 | 87 |
| 10 | 100 | 95 |
| 32 | 104 | 94 |
| 100 | 111 | 93 |

TABLE 12

Effect of AZT on HIV-1 (P2) in PBMC

| AZT (uM) | Toxicity % CC | Efficacy % p24 Reduction |
|---|---|---|
| 0.001 | 100 | 12 |
| 0.003 | 111 | 21 |
| 0.01 | 100 | 14 |
| 0.03 | 99 | 10 |
| 0.10 | 101 | 20 |
| 0.32 | 99 | 26 |
| 1 | 105 | 22 |
| 3 | 105 | 51 |
| 10 | 104 | 77 |

The following Table 13 summarizes the efficacy and toxicity of the antiviral agent of the invention against the HIV virus.

TABLE 13

H2K-1001 (90I) antiviral Activity in T cell lines and PBMC

| Cell Type | Virus | EC50* | IC50* |
|---|---|---|---|
| PBMC | HIV-1RF | $8.00 \times 10^{0}$ | $13.20 \times 10^{0}$ |
| CEM-SS | HIV-1RF | $2.00 \times 10^{-2}$ | $>1.00 \times 10^{2}$ |

*Data presented in ug/ml.

One can observe from the above that the antiviral agent of the invention, H2K-1001 (90i), yielded significant antiviral activity in two separate cell systems. It was active against a highly drug-susceptible laboratory strain of HIV-1 (RF) in an established cell line. We also evaluated the agent's (90i's) activity against a non-nucleoside/nucleoside resistant clinical isolate, P2 in primary peripherial blood mononuclear cells.

A pharmaceutical composition including diethylene glycol dibenzoate, or a structurally-related derivative thereof, may be prepared, in a conventional manner. In particular, a pharmaceutical composition made in accordance with the present invention would include diethylene glycol dibenzoate, or a structural derivative thereof in an amount sufficient to provide therapeutic and/or prophylactic benefit, in combination with one or more pharmaceutically or physiologically acceptable carriers, diluents or excipients. Compositions of the present invention may be formulated for any appropriate manner for administration, including, for example, oral, nasal, intravenous or intramuscular administration. Appropriate dosages, duration and frequency of administration would be determined by known factors, such as the condition of the patient, the type and severity of the disease and the method of administration.

While this invention has been described as having preferred ranges, steps, materials, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

REFERENCE(S)

The following reference(s), to the extent that they provide exemplary procedural or other details supplementary to those set forth herein, are specifically incorporated herein by reference.

Daids Virology Manual for HIV Laboratories, Compiled by The Division of AIDS, National Institute of Allergy and Infectious Diseases, National Institutes of Health and Collaborating Investigators, Version January 1997 (available online at http://www.niaid.nih.gov/daids/vir manual/full vir manual.pdf)

What is claimed is:

1. A method for controlling replication of an immunodeficiency virus, consisting essentially of:
   exposing a cell infected with an immunodeficiency virus to an antiviral agent; and
   wherein the antiviral agent is diethylene glycol dibenzoate.

2. The method of claim 1, wherein:
   the cell comprises a lymphocyte.

3. The method of claim 2, wherein:
   the immunodeficiency virus comprises a human immunodeficiency virus (HIV).

4. The method of claim 1, wherein:
   the cell comprises a CD4+T cell.

5. A method for the treatment of an immunodeficiency condition, consisting essentially of:
   administering to a subject in need thereof an antiviral agent; and
   wherein the antiviral agent is diethylene glycol dibenzoate.

6. The method of claim 5, wherein:
   the immunodeficiency condition comprises acquired immunodeficiency syndrome (AIDS).

7. A method for the treatment of an infection caused by an immunodeficiency virus, consisting essentially of:
   administering to a subject in need thereof an antiviral agent; and
   wherein the antiviral agent is diethylene glycol dibenzoate.

8. The method of claim 7, wherein:
   the immunodeficiency virus comprises a human immunodeficiency virus (HIV).

9. The method of claim 8, wherein:
   the infection comprises acquired immunodeficiency virus syndrome (AIDS).

* * * * *